United States Patent [19]

Roling

[11] Patent Number: 4,797,504

[45] Date of Patent: Jan. 10, 1989

[54] METHOD AND COMPOSITION FOR INHIBITING ACRYLATE ESTER POLYMERIZATION

[75] Inventor: Paul V. Roling, Spring, Tex.

[73] Assignee: Betz Laboratories, Inc., Trevose, Pa.

[21] Appl. No.: 916,267

[22] Filed: Oct. 7, 1986

[51] Int. Cl.⁴ .............................................. C07C 67/62
[52] U.S. Cl. ....................... 560/4; 252/401; 252/403; 562/598
[58] Field of Search .................... 252/401, 403; 560/4; 562/598

[56] References Cited

U.S. PATENT DOCUMENTS

| | | | |
|---|---|---|---|
| 3,408,422 | 10/1968 | May | 260/837 |
| 3,426,063 | 2/1969 | Gros | 560/4 X |
| 3,674,651 | 7/1972 | Otsuki et al. | 203/8 |
| 4,016,198 | 4/1977 | Wilder | 560/4 |
| 4,017,544 | 4/1977 | Mullins | 560/4 X |
| 4,267,365 | 5/1981 | Findeisen | 560/205 |
| 4,480,116 | 10/1984 | Clonce et al. | 560/4 |

FOREIGN PATENT DOCUMENTS 163428  6/1976  Czechoslovakia.
47-18820  9/1972  Japan.

OTHER PUBLICATIONS

Douglas et al., "Screen and Select Vinyl Monomer Inhibitors", Hydrocarbon Processing 6/82, pp. 109–112.

Primary Examiner—Werren B. Lone
Assistant Examiner—Vera C. Clarke
Attorney, Agent, or Firm—Alexander D. Ricci

[57] ABSTRACT

This invention relates to compositions and methods of inhibiting acrylate monomer polymerization at elevated temperatures comprising adding to the acrylate monomer an effective amount for the purpose of (a) a hydroxylamine having the formula

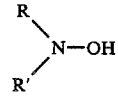

wherein R and R' are the same or different and are hydrogen, alkyl, aryl, alkaryl or aralkyl groups, and (b) a para-phenylenediamine or derivative thereof having at least one N-H group. Preferably the phenylenediamine is a para-phenylenediamine having the formula

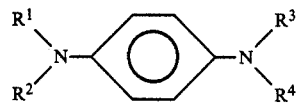

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ is hydrogen.

18 Claims, No Drawings

METHOD AND COMPOSITION FOR INHIBITING ACRYLATE ESTER POLYMERIZATION

BACKGROUND OF THE INVENTION

1. Field of the Invention

This invention relates to a composition and method for use in inhibiting acrylate monomer polymerization at elevated temperatures.

2. Description of the Prior Art

It is well known in the art that acrylate monomers readily polymerize and that the rate of polymerization increases with increasing temperature. Common industrial methods for producing the acrylic monomers typically include purification processes such as distillation to remove impurities. However, purification operations carried out at elevated temperatures result in an increased rate of undesirable polymerization. The polymerization of acrylate monomers is undesirable because it causes fouling of processing equipment and it renders the compounds unfit for use without further treatment.

Known polymerization inhibitors for acrylates include phenothiazine, hydroquinone, the methyl ether of hydroquinone, benzoquinone, and methylene blue. Of primary interest is Japanese Pat. No. 47-18820 which discloses the use of dialkylhydroxylamine of generic structure

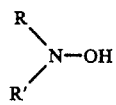

(with R and R' as its alkyl radicals), singly or together with other sundry polymerization inhibitors, to inhibit polymerization of unsaturated compounds of generic structure

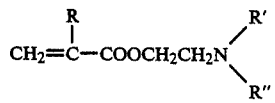

(where R stands for hydrogen or methyl radical and R' and R" for alkyl radicals). Also, May in U.S. Pat. No. 3,408,422 discloses a process for stabilizing ethylenically unsaturated polyesters and a composition stabilized against premature gelation comprising (1) a hydroxy—containing ethylenically unsaturated polyester of a glycidyl polyether of a polyhydric phenol and an ethylenically unsaturated monocarboxylic acid, and (2) a hydroxylamine compound.

Phenylenediamines alone or with oxygen are known in the art as polymerization inhibitors in acrylate systems. Otsuki et al. in U.S. Pat. No. 3,674,651 discloses a process for inhibiting the polymerization of acrylic acid using a combination of diphenylamine or its derivatives and an oxygen-containing gas, or mixtures of diphenylamine or its derivatives with benzoquinone and/or hydroquinone mono-methyl-ether and an oxygen-containing gas. Wilder, in U.S. Pat. No. 4,016,198, discloses a method of inhibiting polymerization of unsaturated carboxylic acid esters and improved unsaturated carboxylic acid ester compositions comprising incorporating into the ester composition a combination of polyalkyleneamines and certain N-aryl-o or p-phenylenediamines. Also, Mullins in U.S. Pat. No. 4,017,544 discloses the use of a class of N-(nitroalkyl)-N'-phenyl-p-phenylenediamines to inhibit the polymerization of unsaturated carboxylic acid esters. Findeisen in U.S. Pat. No. 4,267,365 discloses a process for the preparation of certain oligomeric acrylic acids wherein the acrylic acid is heated in the presence of 0.001 to 1% by weight of a polymerization inhibitor consisting of molecular oxygen, nitric oxide, a phenol, a quinone, an aromatic amine, a nitro compound or diphenylpicrylhydrazyl to a temperature from about 50° to 200° C. Clonce et al. in U.S. Pat. No. 4,480,116 discloses an improved method for preparing and processing readily polymerizable acrylate monomers by employing phenyl-para-benzoquinone, 2,5-diphenyl-para-benzoquinone, or a mixture thereof. None of these prior art references recognizes the unique synergistic mixture of hydroxylamine and phenylenediamine or derivatives thereof having at least one N-H group as desirable for inhibiting acrylate ester polymerization.

SUMMARY OF THE INVENTION

This invention relates to compositions and methods of inhibiting acrylate monomer polymerization at elevated temperatures comprising adding to the acrylate monomer an effective amount for the purpose of (a) a hydroxylamine having the formula

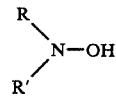

wherein R and R' are the same or different and are hydrogen, alkyl, aryl, alkaryl or aralkyl groups, and (b) a phenylenediamine or derivative thereof having at least one N-H group. Preferably, the phenylenediamine is a para-phenylenediamine having the formula

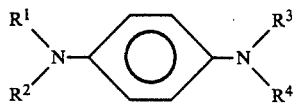

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ are hydrogen. This mixture provides an unexpectedly higher degree of polymerization inhibition of acrylate monomers than the individual ingredients comprising the mixture at elevated temperatures. It is therefore possible to produce a more effective acrylate polymer inhibiting composition and method than is obtainable by the use of either ingredient alone. Because of the enhanced polymer inhibiting activity of the mixture, the concentrations of each of the ingredients may be lowered and the total quantity of the polymerization inhibitor required for an effective treatment at elevated temperatures may be reduced.

Accordingly, it is an object of the present invention to provide compositions and methods for inhibiting the polymerization of acrylate monomers at elevated temperatures. It is another object of this invention to control fouling of processing equipment due to the polymerization. It is a further object of the present invention to provide economically effective polymer inhibiting compositions and methods. These and other objects and advantages of the present invention will be apparent to those skilled in the art upon reference to the following detailed description of the invention, which demonstrates the synergism of the compounds comprising the instant invention.

DETAILED DESCRIPTION OF THE INVENTION

The hydroxylamines used with phenylenediamine or derivatives thereof having at least one N-H group in accordance with the instant invention correspond to the chemical formula:

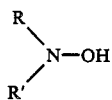

wherein R and R' are the same or different and are hydrogen, alkyl, aryl, alkaryl, or aralkyl groups. The alkyl, alkaryl and aralkyl groups may be straight or branched-chain groups. Preferably, the alkyl, aryl, alkaryl, or aralkyl groups have one to about twenty carbon atoms. Examples of suitable hydroxylamines include N,N-diethylhydroxylamine; N,N-dipropylhydroxylamine; N,N-dibutylhydroxylamine; N,N-butylethylhydroxylamine; N,N-2-ethyl-butryloctylhydroxylamine; N,N-didecylhydroxylamine; N,N-dibenzylhydroxylamine; N-benzylhydroxylamine; N,N-butylbenzylhydroxylamine; N-phenylhydroxylamine; N,N-butylphenylhydroxylamine; methylbenzylhydroxylamines; ethylbenzylhydroxylamines; etc. The term "methylbenzylhydroxylamines" is meant to include mixtures of benzylhydroxylamines and methylbenzylhydroxylamines, such as Mixture B in Table III described below. Also, the term "ethylbenzylhydroxylamines" is meant to include mixtures of benzylhydroxylamines, such as Mixture A in Table III described below. Most preferably, the hydroxylamine is selected from the group consisting of N,N-diethylhydroxylamine, N,N-dibenzylhydroxylamine, methylbenzylhydroxylamines, and ethylbenzylhydroxylamines.

The phenylenediamine component of the inhibitor mixtures of this invention include phenylenediamine and derivatives thereof having at least one N-H group. It is thought that ortho-phenylenediamine or derivatives thereof having at least one N-H group are suitable for use in accordance with the instant invention. However, the preferred phenylenediamine is para-phenylenediamine having the formula

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ is hydrogen. More preferably, the alkyl, aryl, alkaryl and aralkyl groups have one to about twenty carbon atoms. The alkyl, alkaryl and aralkyl groups may be straight or branched-chain groups. Exemplary para-phenylenediamines include p-phenylenediamine wherein $R^1$, $R^2$, $R^3$ and $R^4$ are hydrogen; N,N,N'-trialkyl-p-phenylenediamines, such as N,N,N'-trimethyl-p-phenylenediamine, N,N,N'-triethylphenylene-p-diamine, etc.; N,N-dialkyl-p-phenylenediamines, such a N,N-dimethyl-p-phenylenediamine, N,N-diethyl-p-phenylenediamine, etc.; N-phenyl-N',N'-dialkyl-p-phenylenediamines such as N-phenyl-N'-N'-dimethyl-p-phenylenediamine, N-phenyl-N',N'-diethyl-p-phenylenediamine, N-phenyl-N',N',-dipropyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine, N-phenyl-N'-methyl-N'-propyl-p-phenylenediamine, etc.; N-phenyl-N'-alkyl-p-phenylenediamines, such as N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-butyl-p-phenylenediamine, N-phenyl-N'-isobutyl-p-phenylenediamine, N-phenyl-N'-isobutyl-p-phenylenediamine, N-phenyl-N'-sec-butyl-p-phenylenediamine, N-phenyl-N'-tert-butyl-p-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine, etc. Preferably, the para-phenylenediamine is selected from the group consisting of N-phenyl-N'-(1,3-dimethylbutyl)-p-phenylenediamine, N-phenyl-N'-(1,4-dimethylpentyl)-p-phenylenediamine, and para-phenylenediamine wherein $R^1$, $R^2$, $R^3$ and $R^4$ are hydrogen.

The present invention is applicable to readily polymerizable acrylate monomers. The term "acrylate monomer" as used herein is intended to include acrylic acid, methacrylic acid and the various esters of acrylic acid and methacrylic acid. Such acrylate esters can include n-alkyl, secondary and branched-chain alkyl esters of acrylic acid and methacrylic acid. Exemplary esters of acrylic acid include methyl acrylate, ethyl acrylate, propyl acrylate, isopropyl acrylate, n-butyl acrylate, isobutyl acrylate, sec-butyl acrylate, 2-methylbutylacrylate, 3-methylbutyl acrylate, 2-ethylbutyl acrylate, 1,3-dimethylbutyl acrylate, pentyl acrylate, hexyl acrylate, 2-ethylhexyl acrylate, heptyl acrylate, 1-methylheptyl acrylate, octyl acrylate, decyl acrylate, dodecyl acrylate, hexadecyl acrylate, etc. Exemplary esters of methacrylic acid include methyl methacrylate, ethyl methacrylate, propyl methacrylate, isopropyl methacrylate, butyl methacrylate, isobutyl methacrylate, sec-butyl methacrylate, tert-butyl methacrylate, hexyl methacrylate, octyl methacrylate, isooctyl methacrylate, 2-ethylhexyl methacrylate, decyl methacrylate, etc. Preferably, the acrylate ester is n-butyl acrylate.

The total amount of hydroxylamine and phenylenediamine or derivatives thereof having at least one N-H group used in the compositions and methods of the present invention as a polymerization inhibitor is that amount which is sufficient to effect inhibition of polymerization and will, of course, vary according to the particular acrylate monomer and conditions under which it is used. At higher temperatures, larger amounts are generally required. Preferably, the total amount of hydroxylamine and phenylenediamine or derivatives thereof having at least one N-H group is from about 1 ppm to about 10,000 ppm based upon the weight of the acrylate monomer. Most preferably, the total amount of the aforesaid compounds is from about 1 ppm to about 1000 ppm based upon the weight of the acrylate monomer. The relative concentrations of hydroxylamine and phenylenediamine or derivatives thereof having at least one N-H group are generally in the range of about 5 to about 95 weight percent hydroxylamine and about 95 to about 5 weight percent phenylenediamine or derivatives thereof having at least one N-H group based on the total combined weight of these components. Preferably, the molar ratio of hydroxylamine to phenylenediamine or derivatives thereof having at least one N-H group is about 1:10 to about 10:1 and, most preferably, the molar ratio is about 1:5 to about 5:1.

The term "elevated temperatures" as used herein means temperatures at and above the boiling point of the particular acrylate monomer utilized. Of course, since the boiling points of the various acrylate monomers are different, the elevated temperatures will vary depending upon the boiling point of the particular acrylate monomer utilized at the particular pressure at which the acrylate monomer is added. For example, the boiling point of n-butyl acrylate is about 294° F. at 760 mm pressure, so the elevated temperature for n-butyl acrylate would be 294° F. and above at 760 mm pressure.

The methods and compositions of the present invention can control the fouling of processing equipment, such as equipment used in the separation and purification processes of acrylate monomers, which is due to or caused by the polymerization of the acrylate monomers. The instant invention is useful as a process inhibitor, which is employed during the preparation and processing of the acrylate monomer. The invention can be utilized under normal pressure (760 mm), under superatmospheric pressure or under reduced pressure. The hydroxylamine and phenylenediamine or derivatives thereof can be provided to the acrylate monomer by any conventional method. The components can be added to the acrylate monomer as a single composition containing the inhibitor compounds or the individual components can be added separately or in any other desired combination. The composition may be added as either a concentrate or as a solution using a suitable carrier solvent which is compatible with the acrylate monomer.

To demonstrate the synergism which is provided by the inventive combination of compounds, the data set forth below was developed. The following examples are included as being illustrations of the invention and should not be construed as limiting the scope thereof.

EXAMPLES

Polymerization inhibition of n-butyl acrylate was evaluated by the reflux test method. A round-bottom flask equipped with a condenser, a magnetic stirrer, and gas inlet and outlet tubes was flushed with nitrogen for ten minutes. Freshly distilled n-butyl acrylate (20 mL-vacuum distilled at about 40° C. to remove MEHQ inhibitor) with the additive being tested was added to the flask and the apparatus was again flushed with nitrogen for ten minutes. The mixture was heated at reflux (294° F.) for two hours whereupon a 10 mL aliquot of the mixture was added to 90 mL of methanol in a calibrated centrifuge tube. The amount of polymeric liquid that settled was recorded. The less polymer observed, the more effective the treatment. The results are reported in Table I below. It is believed that the fluctuations in the mL of polymer for the lower dosages in Table I may have been due to a malfunctioning pipette that was determined to be over-dosing at the low dosages after most of these experiments were conducted.

TABLE I

| PDMBPDA ppm | DEHA ppm | No. Tests | mL Polymer | Ave. mL Polymer |
|---|---|---|---|---|
| 25 | 0 | 4 | 2.3, 3.0, 3.5, 5.5 | 3.6 |
| 0 | 25 | 4 | 4.5, 3.5, 3.5, 3.3 | 3.7 |
| 12.5 | 12.5 | 1 | 0.03 | 0.03 |
| 10 | 15 | 1 | 4.5$^a$ | 4.5$^a$ |
| 10 | 15 | 11 | 2.8, 0, 0.5, 0, 0, 0, 0, 0, 0, 0, 1.6 | 0.4 |
| 12 | 0 | 2 | 0.5, 2.9 | 1.7 |
| 8 | 0 | 1 | 4.3 | 4.3 |
| 0 | 16 | 1 | 3.3 | 3.3 |
| 0 | 12 | 1 | 1.9 | 1.9 |
| 0 | 10 | 1 | 1.9 | 1.9 |
| 9 | 3 | 1 | 0 | 0 |
| 6 | 6 | 2 | 0, 0.5 | 0.25 |
| 3 | 9 | 1 | 0.1 | 0.1 |
| 0 | 0 | 3 | $^b$ | $^b$ |

PDMBPDA = N—phenyl-N'—(1,3-dimethylbutyl)-p-phenylenediamine
DEHA = N,N—diethylhydroxylamine
$^a$This data point was generated during one of the very first experiments that were run using the above-described reflux test method and the technician conducting the experiment was still learning the technique; therefore, it is believed that this data point is inaccurate, especially in view of the further data generated using 10 ppm PDMBPDA and 15 ppm DEHA reported above.
$^b$Mixture became so viscous that it was not possible to obtain a 10 mL aliquot.

The results reported in Table I indicate that combinations of N-phenyl-N'(1,3-dimethylbutyl)-p-phenylenediamine and N,N-diethylhydroxylamine showed a synergistic effect in inhibiting polymerization at elevated temperatures.

Further tests were conducted using other phenylenediamines (PDA) and hydroxylamines ($R_2NOH$). These tests used the procedure described above for Table I data and the results are reported in Table II below.

TABLE II

| PDA | ppm | $R_2PNOH$ | ppm | mL Polymer in 2 Hrs. |
|---|---|---|---|---|
| PDMPPDA | 25 | None | — | 3.0 |
| PDMPPDA | 12.5 | N,N—diethylhydroxylamine | 12.5 | 0.0 |
| p-PDA | 25 | None | — | a |
| p-PDA | 12.5 | N,N—diethylhydroxylamine | 12.5 | 0.0 |
| TMPDA | 25 | None | — | a |
| TMPDA | 12.5 | N,N—diethylhydroxylamine | 12.5 | a |
| PDMBPDA + p-PDA | 12.5 + 12.5 | None | — | a |
| None | — | N,N—dibenzylhydroxylamine | 25 | a |
| PDMBPDA | 12.5 | N,N—dibenzylhydroxylamine | 12.5 | 0.03 |
| None | — | N,N—diethylhydroxylamine + N,N—dibenzylhydroxylamine | 12.5 + 12.5 | a | a Mixture became thick and viscous and removal of an aliquot was impractical.
PDMPPDA = N—phenyl-N'—(1,4-dimethylpentyl)-p-phenylenediamine
p-PDA = p-phenylenediamine [$C_6H_4(NH_2)_2$]
TMPDA = N,N,N',N',—tetramethyl-p-phenylenediamine
PDMBPDA = N—phenyl-N'—(1,3-dimethylbutyl)-p-phenylenediamine The results reported in Table II indicate that N-phenyl-N'-(1,4-dimethylpentyl)-p-phenylenediamine and p-phenylenediamine [$C_6H_4(NH_2)_2$], both of which have N-H groups, exhibited synergism in inhibiting polymerization when used in combination with N,N-diethylhydroxylamine at elevated temperatures. However, the phenylenediamine without a N-H group, N,N,N'N'-tetramethyl-p-phenylenediamine, failed to show synergism with N,N-diethylhydroxylamine. Also, another hydroxylamine, N,N-dibenzylhydroxylamine, showed synergism when used in combination with N-phenyl-N'-(1,3-dimethylbutyl)-p-phenylenediamine. But the test runs where two phenylenediamines and two hydroxylamines were used respectively showed no synergism.

Additional testing was conducted to further evaluate the synergistic combination of the instant invention utilizing the reflux test method described above. Two mixtures were prepared for these additional tests. Mixture A was prepared by placing 15.9 g (0.15 mol) of anhydrous sodium carbonate, 7.0 g (0.1 mol) of hydroxylamine hydrochloride, 11.5 mL (12.5 g, 0.1 mol) of benzyl chloride, 15 mL (16 g, 0.1 mol) of ethylbenzyl chlorides (about 30% ortho and 70% para isomers) and 130 mL of methanol in a 1-L round-bottomed flask. This mixture was heated and stirred at reflux for four hours, whereupon the methanol was removed by distillation. The remaining viscous mixture was stirred with 50 mL of water to yield a clear, colorless aqueous layer and a hazy organic layer. Separation of the layers resulted in 22.8 g (98% of theory) of crude dibenzylhydroxylamines (by gas chromatography—mass spectrometry analysis this mixture consists of N-monobenzylhydroxylamine, N-monoethylbenzylhydroxylamine, N,N-dibenzylhydroxylamine, N-benzyl-N-ethylbenzylhydroxylamine, and N,N-diethylbenzylhydroxylamine, plus other unidentified materials). The starting chlorides were virtually not present in the resulting product. Acidification of the barely basic aqueous layer yielded substantially no $CO_2$. Mixture B was prepared using the same procedure as described above for preparation of Mixture A, but 6.3 (0.05 mol) benzyl chloride, 7.0 g (0.05 mol) of o-methylbenzyl chloride, 7.0 g (0.5 mol) of m-methylbenzyl chloride, and 7.0 g (0.05 mol) of p-methylbenzyl chloride were used in place of the benzyl and ethylbenzyl chlorides, resulting in 20.5 g (87%) yield of N-monobenzylhydroxylamine, N-monomethylbenzylhydroxylamine, N,N-dibenzylhydroxylamine, N-benzyl-N-methylbenzylhydroxylamine, and N,N-dimethylbenzylhydroxylamine, plus other unidentified materials. The results are reported in Table III below.

TABLE III

| PDMBPDA ppm | Hydroxylamine ppm | Molar Ratio PDMBPDA: Hydroxylamine | mL Polymer |
|---|---|---|---|
| 25 | None | — | 5.0 |
| 23 | 2 DEHA | 4:1 | 1.5 |
| 21 | 4 DEHA | 2:1 | 0 |
| 19 | 6 DEHA | 1:1 | 0 |
| 15 | 10 DEHA | 1:2 | 0 |
| 11 | 14 DEHA | 1:4 | 0 |
| 20 | 5 Mixture A | 4:1 | 4.0 |
| 17 | 8 Mixture A | 2:1 | 3.5 |
| 13 | 12 Mixture A | 1:1 | 1.5, 2.0 |
| 19 | 19 Mixture A | 1:1 | a |
| 9 | 16 Mixture A | 1:2 | a |
| 5 | 20 Mixture A | 1:4 | a |
| 0 | 25 Mixture A | — | a, a, 4.5 |
| 20 | 5 Mixture B | 4:1 | a |
| 17 | 8 Mixture B | 2:1 | 1.9 |
| 13 | 12 Mixture B | 1:1 | 0, 2.0 |
| 19 | 19 Mixture B | 1:1 | 0.5 |
| 10 | 15 Mixture B | 1:2 | 0.1, 0.15 |
| 9 | 16 Mixture B | 1:2 | 0.5 |
| 5 | 20 Mixture B | 1:4 | a |
| 0 | 25 Mixture B | — | a, 2.4 | a Mixture became too viscous to be able to remove a 10-mL aliquot.
PDMBPDA = N—phenyl-N'—(1,3-dimethylbutyl)-p-phenylenediamine
DEHA = N,N—diethylhydroxylamine Polymerization inhibition of n-butyl acrylate was also evaluated by the viscosity test method, using an oil bath regulated at 285° F. with a Thermo-Watch. Double distilled (under vacuum at about 35° C. with about 12 inches distance from the flask to the condenser) n-butyl acrylate (10.0 mL) was placed in a 17 mL tube and 50 uL of 0.25 wt% xylene solutions of additives were added. The tubes were capped with a rubber septum, which was wired on. Two needles were inserted in the septum and argon was purged through for 30 sec., whereupon the needles were removed. The tubes were then placed in the oil bath and the viscosities of the solutions measured at appropriate times by inverting the tube and observing the time needed for the 7 mL bubble to reach the top of the inverted tube. The time required to obtain a viscosity of 20 sec. was calculated for each tube by interpolating between the two points that bracketed the 20 sec. viscosity using a semilog evaluation. If a viscosity of 20 was not reached in 5 days of testing, the data were extrapolated to obtain the time to reach a viscosity of 20 sec. If the reaction proceeded so fast that a viscosity of 20 sec. was missed, again the first two viscosity points were extrapolated to obtain the time to a viscosity of 20 sec. The viscosity at the beginning of the test period was less than 1 sec. Usually two to five viscosity determinations were made per tube. The results are reported in Table IV below.

TABLE IV

| Additive | mL of Air | Time (a) |
|---|---|---|
| None | 0 | 112, 121 |
| DEHA | 0 | 114, 113 |
| PDMBPDA | 0 | 1258, 886 |
| DEHA (25 ppm) & PDMBPDA (25 ppm) | 0 | 416, 935 |
| None | 0.2 | 137, 125 |
| DEHA | 0.2 | 115, 113 |
| PDMBPDA | 0.2 | 1271, 675 |
| DEHA (25 ppm) & PDMBPDA (25 ppm) | 0.2 | 2052, 1784 |

(a) Values for None and DEHA only were approximated from one point using relative viscosity = 1 at time = 1 as the other point.
DEHA = N,N—diethylhydroxylamine
PDMBPDA = N—phenyl-N'—(1,3-dimethylbutyl)-p-phenylenediamine While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method of inhibiting acrylate monomer polymerization at elevated temperatures comprising adding to the acrylate monomer an effective amount of (a) a hydroxylamine having the formula

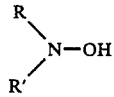

wherein R and R' are the same or different and are hydrogen, alkyl, aryl, alkaryl or aralkyl groups and (b) a phenylenediamine or derivative thereof having at least one N-H group.

2. The method according to claim 1 wherein the alkyl, aryl, alkaryl and aralkyl groups have one to about twenty carbon atoms.

3. The method according to claim 2 wherein the total amount of the hydroxylamine and the phenylenediamine is from about 1 ppm to about 10,000 ppm based upon the weight of the acrylate monomer.

4. The method according to claim 2 wherein the molar ratio of the hydroxylamine to the phenylenediamine is about 1:10 to about 10:1.

5. A method of inhibiting acrylate monomer polymerization at elevated temperatures comprising adding to the acrylate monomer an effective amount of (a) a hydroxylamine having the formula

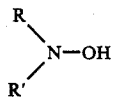

wherein R and R' are the same or different and are hydrogen, alkyl, aryl, alkaryl or aralkyl groups, and (b) a para-phenylenediamine having the formula

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ is hydrogen.

6. The method according to claim 5 wherein the alkyl, aryl, alkaryl and aralkyl groups have one to about twenty carbon atoms.

7. The method according to claim 6 wherein the hydroxylamine is selected from the group consisting of N,N-diethylhydroxylamine, N,N-dibenzylhydroxylamine, methylbenzylhydroxylamines, and ethylbenzylhydroxylamines.

8. The method according to claim 7 wherein the para-phenylenediamine is selected from the group consisting of N-phenyl-N'-(1,3-dimethylbutyl)-p-phenylenediamine. N-phenyl-N'-(1,4-dimethylpentyl)-p-phenylenediamine, and para-phenylenediamine wherein $R_1$, $R_2$, $R_3$, and $R_4$ are hydrogen.

9. The method according to claim 6 or 8 wherein the molar ratio of the hydroxylamine to the para-phenylenediamine is about 1:5 to about 5:1.

10. The method according to claim 6 or 8 wherein the total amount of the hydroxylamine and the para-phenylenediamine is from about 1 ppm to about 10,000 ppm based upon the weight of the acrylate monomer.

11. The method according to claim 10 wherein the acrylate monomer is n-butyl acrylate.

12. A composition to inhibit acrylate monomer polymerization at elevated temperatures comprising the acrylate monomer and an effective amount of (a) a hydroxylamine having the formula

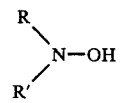

wherein R and R' are the same or different and are hydrogen, alkyl, aryl, alkaryl or aralkyl groups, and (b) a para-phenylenediamine having the formula

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ is hydrogen.

13. The composition according to claim 12 wherein the alkyl, aryl, alkaryl and aralkyl groups have one to about twenty carbon atoms.

14. The composition according to claim 13 wherein the hydroxylamine is selected from the group consisting of N,N-diethylhydroxylamine, N,N-dibenzylhydroxylamine, methylbenzylhydroxylamines, and ethylbenzylhydroxylamines.

15. The composition according to claim 14 wherein the para-phenylenediamine is selected from the group consisting of N-phenyl-n'-(1,3-dimethylbutyl)-p-phenylenediamine, N-phenyl-N'-(1,4-dimethylpentyl)-p-phenylenediamine, and para-phenylenediamine wherein $R^1$, $R^2$, $R^3$ and $R^4$ are hydrogen.

16. The composition according to claim 13 or 15 wherein the molar ratio of the hydroxylamine to the para-phenylenediamine is about 1:10 to about 10:1.

17. The composition according to claim 13 or 15 wherein the total amount of the hydroxylamine and the para-phenylenediamine is from about 1 ppm to about 10,000 ppm based upon the weight of the acrylate monomer.

18. The composition according to claim 17 wherein the acrylate monomer is n-butyl acrylate.

* * * * *